United States Patent
Sakamoto (10) Patent No.: US 8,998,619 B2
(45) Date of Patent: Apr. 7, 2015

(54) CABLE CONNECTOR AND ENDOSCOPE APPARATUS

(71) Applicant: FUJIFILM Corporation, Tokyo (JP)

(72) Inventor: Toshio Sakamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 94 days.

(21) Appl. No.: 13/778,956

(22) Filed: Feb. 27, 2013

(65) Prior Publication Data

US 2013/0244453 A1  Sep. 19, 2013

(30) Foreign Application Priority Data

Mar. 13, 2012 (JP) ................................. 2012-055535

(51) Int. Cl.
| | |
|---|---|
| *H01R 12/00* | (2006.01) |
| *H05K 1/00* | (2006.01) |
| *H01R 12/71* | (2011.01) |
| *A61B 1/00* | (2006.01) |
| *A61B 1/005* | (2006.01) |
| *H01R 12/53* | (2011.01) |
| *H01R 12/72* | (2011.01) |
| *A61B 1/05* | (2006.01) |

(52) U.S. Cl.
CPC .......... *H01R 12/712* (2013.01); *A61B 1/00124* (2013.01); *A61B 1/005* (2013.01); *H01R 12/53* (2013.01); *H01R 12/721* (2013.01); *A61B 1/05* (2013.01)

(58) Field of Classification Search
CPC .... H01R 12/712; H01R 12/53; H01R 12/721; H01R 12/71; A61B 1/00124; A61B 1/005; A61B 1/05; A61B 1/00
USPC .............. 439/55, 76.1, 81; 600/463, 462, 132
See application file for complete search history.

(56) References Cited

U.S. PATENT DOCUMENTS

| | | | |
|---|---|---|---|
| 2005/0143658 A1 | 6/2005 | Saiga | |
| 2005/0143659 A1 | 6/2005 | Saiga | |
| 2013/0244456 A1* | 9/2013 | Sakamoto | ........................ 439/81 |

FOREIGN PATENT DOCUMENTS

| | | | |
|---|---|---|---|
| JP | 2005-192639 A | 7/2005 | |
| JP | 2005-192640 A | 7/2005 | |

* cited by examiner

*Primary Examiner* — Javaid Nasri (74) *Attorney, Agent, or Firm* — Birch, Stewart, Kolasch & Birch, LLP (57) ABSTRACT

A cable connector includes a circuit board, having a predetermined width in a manner passable through an elongated tube of an endoscope apparatus, disposed to extend in an axial direction. A terminal group is formed on the circuit board, for electrically contacting a socket connector. First and second land patterns are formed on the circuit board, arranged in the axial direction so that the terminal group is disposed therebetween, wherein a front end of a first electric line group having lines among electric lines of a cable structure is electrically coupled to the first land pattern, and a front end of a second electric line group having lines among the electric lines is coupled to the second land pattern. A wiring pattern is formed on the circuit board, for electrically coupling the first land pattern to the terminal group and coupling the second land pattern to the terminal group.

9 Claims, 10 Drawing Sheets

CABLE CONNECTOR AND ENDOSCOPE APPARATUS

BACKGROUND OF THE INVENTION

1. Field of the Invention

The present invention relates to a cable connector and an endoscope apparatus. More particularly, the present invention relates to a cable connector and an endoscope apparatus, in which a high number of electric lines of a cable structure can be coupled for electrical connection in a simplified structure and safely without problems in transmitting operation.

2. Description Related to the Prior Art

An endoscope apparatus includes an elongated tube, a tip device and a circuit device or electrical device. The elongated tube is entered in a body cavity of a patient's body to be diagnosed. The tip device is disposed at a distal end of the elongated tube. The circuit device is contained in the tip device or disposed behind the tip device. Examples of the circuit device are a camera module, imaging unit or ultrasonic transducer. A cable structure is connected with the circuit device and extends in an axial direction. The cable structure includes numerous electric lines, which are connected to a control unit disposed in the outside of the body. The circuit device is controlled and driven by the control unit.

A flexible tube device is included in the elongated tube, and dispose to extend from the tip device. The tip device is a part originally separate from the flexible tube device. In the assembling operation, the circuit device is contained the tip device at first. The cable structure from the circuit device is passed through the flexible tube device. Then the flexible tube device is connected with the tip device.

The cable structure passes through the flexible tube device on the elongated tube. It is extremely difficult to connect each one of the electric lines in the cable structure to the control unit after passage through the flexible tube device. If the electric lines are connected with a mechanical part with a larger width than an inner diameter of the elongated tube, maintenance of the endoscope apparatus is very hard. This is because the cable structure can be removed from the flexible tube device only after cutting the electric lines from the mechanical part.

A cable connector or board connector at an end of the cable structure is disclosed in U.S. Pat. Pub. No. 2005/143,658 (corresponding to JP-A 2005-192640) and U.S. Pat. Pub. No. 2005/143,659 (corresponding to JP-A 2005-192639). The cable connector includes conductive lands in a land pattern, terminals in a terminal group, and a wiring pattern. The land pattern is used for connection of the electric lines of the cable structure. The terminal group is connectable to a mating connector for coupling with the cable connector. The wiring pattern wires the land pattern to the terminal group. The cable connector is coupled with the mating connector, to facilitate connective coupling and decoupling of the cable structure even after penetration of the cable structure in the elongated tube.

In the cable connector according to the above documents, the land pattern is single, to which all of the electric lines are connected in a concentrated manner. There arises a problem in which conductive lands are disposed extremely close to each other. Difficulty in coupling the electric lines to the conductive lands is very high. Also, conductive lines in the wiring pattern are extremely near to each other. Thus, breakage of lines, short-circuiting and electric noise are likely to occur seriously. If the number of the electric lines for connection to the cable connector is lowered and the number of the cable connector is increased for safe disposition of the conductive lines or conductive lands, then another problem arises in low operability in mounting the cable structure in the flexible tube device of the elongated tube.

SUMMARY OF THE INVENTION

In view of the foregoing problems, an object of the present invention is to provide a cable connector and an endoscope apparatus, in which a high number of electric lines of a cable structure can be coupled for electrical connection in a simplified structure and safely without problems in transmitting operation.

In order to achieve the above and other objects and advantages of this invention, a cable connector for an endoscope apparatus is provided, the endoscope apparatus including a flexible elongated tube for extending in an axial direction, a circuit device incorporated in the elongated tube, a cable structure, having plural electric lines, contained in the elongated tube, connected with the circuit device, wherein the cable connector is mounted on the cable structure, and couplable with an external socket connector for externally transmitting a signal from the circuit device. The cable connector includes a circuit board, having a width in a manner passable through the elongated tube, disposed to extend in the axial direction. A terminal group of plural terminals is formed on the circuit board, for electrically contacting the socket connector. First and second land patterns are positioned apart from one another in the axial direction, so disposed that the terminal group is positioned therebetween at least partially, for electrical conduction to the electric lines. A wiring pattern is formed on the circuit board, for electrically coupling the first land pattern to the terminal group and electrically coupling the second land pattern to the terminal group.

The first land pattern is disposed on a side of a first board end of the circuit board from the terminal group in the axial direction. The second land pattern is disposed on a side of a second board end of the circuit board from the terminal group in the axial direction. The terminal group is constituted in the axial direction by a first terminal on the side of the first board end, and a second terminal on the side of the second board end. The wiring pattern is constituted in the axial direction by a first conductive line on the side of the first board end, and a second conductive line on the side of the second board end. The first conductive line couples the first terminal to the first land pattern. The second conductive line couples the second terminal to the second land pattern.

The elongated tube includes a flexible tube device for extending in the axial direction. A tip device is mounted on a tip end of the flexible tube device. The tip device is attached to the flexible tube device after the cable structure is entered through the flexible tube device.

The terminals in the terminal group are arranged in the axial direction.

The terminal group and the socket connector are moved relatively toward one another transversely to the axial direction, for contact of the terminal group with the socket connector.

The terminals are arranged along a first longer side line of the circuit board, and the wiring pattern is disposed between the terminal group and a second longer side line of the circuit board.

Furthermore, a pair of cutouts are formed in the circuit board, disposed on the first longer side line so that the terminal group is positioned therebetween, for receiving the socket connector upon entry of the terminal group in the socket connector, to prevent interference with the circuit board.

The cutouts are so shaped that a width thereof decreases toward a center portion of the circuit board from the longer side line.

Furthermore, a third land pattern is disposed beside an intermediate terminal among the terminals in the axial direction and along the second longer side line of the circuit board, for electric coupling to the electric lines. A second wiring pattern is disposed between the third land pattern and the intermediate terminal, for electrically coupling the intermediate terminal to the third land pattern.

In another preferred embodiment, the circuit board includes upper and lower surfaces. The upper surface has the first and second land patterns, and a third land pattern disposed on the side of the second board end from the second land pattern in the axial direction. The lower surface has a second terminal group disposed opposite to the terminal group, and a second wiring pattern for coupling the third land pattern to the second terminal group.

In one preferred embodiment, the circuit board includes upper and lower surfaces. The upper surface has the first and second land patterns, and a third land pattern disposed on the side of the first board end from the first land pattern in the axial direction. The lower surface has a second terminal group disposed opposite to the terminal group, and a second wiring pattern for coupling the third land pattern to the second terminal group.

In still another preferred embodiment, the cable structure includes a first line group of electric lines electrically coupled to the first land pattern on the side of the second board end, and a second line group of electric lines electrically coupled to the second land pattern on the side of the second board end. Furthermore, a flexible circuit board constitutes at least a portion of at least one of the first and second line groups.

Furthermore, a tab portion is formed at the first board end, for enabling portions of the circuit board to pass safely through the elongated tube in penetration thereof.

The tab portion has a width decreasing in the axial direction on the side of the first board end.

The tab portion is a portion of the circuit board.

Furthermore, a flexible wiring board is disposed to extend at least partially between the first and second board ends, and bent substantially in a U shape. The circuit board includes a first portion having the first land pattern. A second portion is opposed to the first portion, and having the second land pattern and the terminal group.

Furthermore, a rigid portion is disposed in the circuit board at least partially, and has the terminal group thereon.

The electric lines include a power supply line for driving the circuit device. A signal line transmits and/or receives the signal with the circuit device. The power supply line is coupled to the first land pattern, and the signal line being coupled to the second land pattern.

Two or more connection mechanisms are arranged on the circuit board in the axial direction, each of the connection mechanisms having the terminal group, the first and second land patterns and the wiring pattern.

Also, furthermore, a retainer retains a portion of the front end of the cable structure to a rear board end of the circuit board.

The third land pattern is disposed between the first and second land patterns.

In one preferred embodiment, furthermore, a ridge projection is disposed to project from an upper surface of the circuit board in an upward direction. A terminal slot is formed in the ridge projection, has the terminal group formed internally, for coupling with the socket connector in the upward direction.

In another preferred embodiment, furthermore, a cutout is formed in the circuit board, disposed between the terminal group and the second land pattern, for receiving a wall of the socket connector upon entry of the terminal group in the socket connector, to prevent interference with the circuit board.

One of the first and second land patterns is arranged with the terminal group in a transverse direction of the circuit board.

The endoscope apparatus further includes a cover tube, disposed to extend from the handle device, for containing the universal cable portion.

The endoscope apparatus further includes a light guide device, covered by the cover tube, for transmitting light from a light source toward the tip device.

The predetermined width of the circuit board is a value in a manner passable through the cover tube.

Also, a cable connector for an endoscope apparatus is provided, the endoscope apparatus including an elongated tube for extending in an axial direction, a circuit device incorporated in the elongated tube, a cable structure, having plural electric lines, contained in the elongated tube, connected with the circuit device, for transmitting a signal, wherein the cable connector is mounted on a front end of the cable structure, couplable with an external socket connector, for transmitting the signal. The cable connector includes a circuit board, having a predetermined width in a manner passable through the elongated tube, disposed to extend in the axial direction. A terminal group is formed on the circuit board, for electrically contacting the socket connector. First and second land patterns are formed on the circuit board, arranged in the axial direction so that the terminal group is disposed therebetween, wherein a front end of a first electric line group having lines among the electric lines is electrically coupled to the first land pattern, and a front end of a second electric line group having lines among the electric lines is electrically coupled to the second land pattern. A wiring pattern is formed on the circuit board, for electrically coupling the first land pattern to the terminal group and electrically coupling the second land pattern to the terminal group.

Also, an endoscope apparatus is provided, including a flexible elongated tube for extending in an axial direction, a circuit device incorporated in the elongated tube, a cable structure, having plural electric lines, contained in the elongated tube, connected with the circuit device, and a cable connector mounted on the cable structure, and couplable with an external socket connector for externally transmitting a signal from the circuit device. The endoscope apparatus has the cable connector including a circuit board, having a width in a manner passable through the elongated tube, disposed to extend in the axial direction. A terminal group of plural terminals, formed on the circuit board, for electrically contacting the socket connector. First and second land patterns are positioned apart from one another in the axial direction, so disposed that the terminal group is positioned therebetween at least partially, for electrical conduction to the electric lines. A wiring pattern is formed on the circuit board, for electrically coupling the first land pattern to the terminal group and electrically coupling the second land pattern to the terminal group.

Furthermore, a handle device is mounted on the elongated tube. A universal cord device has first and second ends, the first end being coupled to the handle device, the second end operating for external connection. A connector shell is disposed at the second end. The cable structure with the cable connector is penetrated through the handle device and the universal cord device, for coupling with the socket connector through the connector shell.

The circuit device is an imaging unit for detecting object light from a body cavity.

Therefore, a high number of electric lines of a cable structure can be coupled for electrical connection in a simplified structure and safely without problems in transmitting operation, because the first and second land patterns are disposed discretely from one another for electrical coupling.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
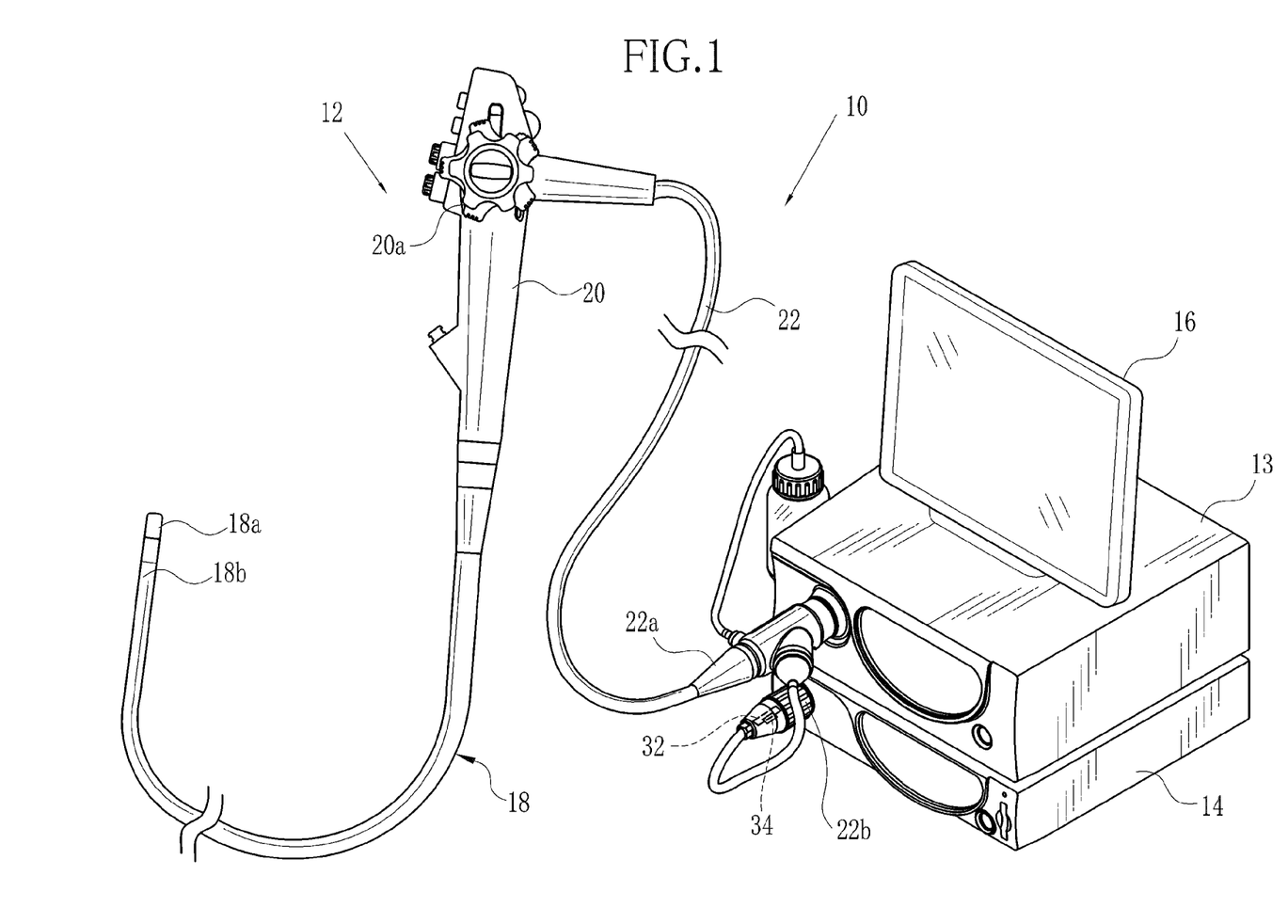
FIG. 1 is a perspective view illustrating an endoscope system.

In FIG. 1, an endoscope system 10 includes an electronic endoscope apparatus 12, a light source apparatus 13, a processing apparatus 14 and a monitor display panel 16. The endoscope apparatus 12 includes an elongated tube 18 and a handle device 20. The elongated tube 18 is entered in a body cavity of a patient, for example, gastrointestinal tract. The handle device 20 is disposed at a proximal end of the elongated tube 18. A universal cord device 22 extends from the handle device 20 for connection to the light source apparatus 13 and the processing apparatus 14.

A light source is incorporated in the light source apparatus 13. The elongated tube 18 has a tip device 18a. Light from the light source is guided by a light guide device extending through the universal cord device 22, the handle device 20 and the elongated tube 18 toward the tip device 18a, which emits the light in a distal direction.

A camera module 24 as circuit device or electrical device is incorporated in the tip device 18a of the elongated tube 18, and is an imaging unit having components of a lens system, an image sensor and the like. Steering wheels 20a are disposed on the handle device 20 for bending the elongated tube 18 up and down and to the right and left. When the steering wheels 20a are rotated, a direction of the tip device 18a for imaging with the camera module 24 is adjusted.

Figure 2:
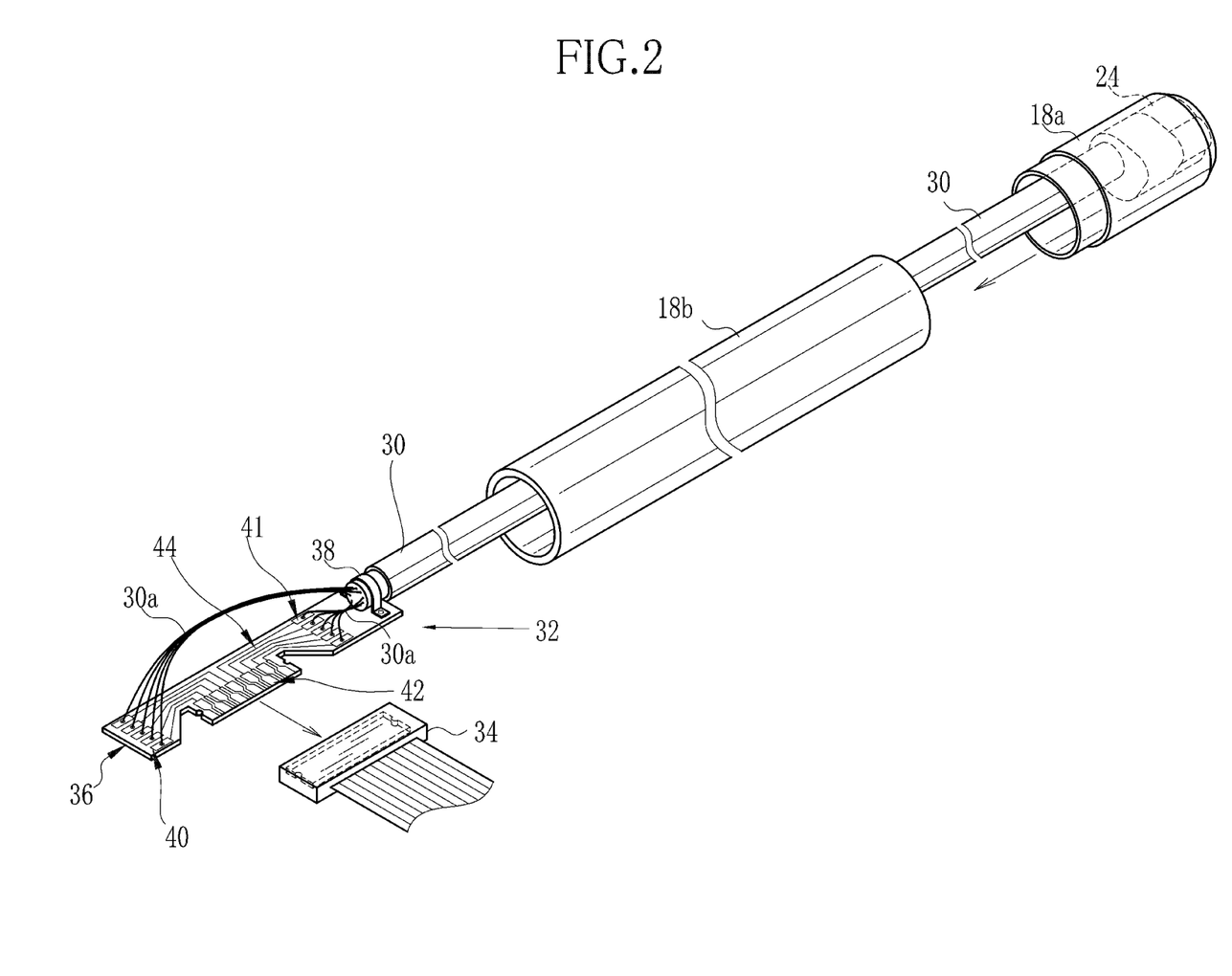
FIG. 2 is a perspective view illustrating a cable connector.

A cable structure 30 or line device of FIG. 2 extends from the camera module 24. The cable structure 30 penetrates through the elongated tube 18, the handle device 20 and the universal cord device 22. There are connector shells 22a and 22b at the front end of the universal cord device 22. A universal cable portion of the cable structure 30 extends toward the inside of the connector shells 22a and 22b. A socket connector 34 or mating connector is disposed in the connector shell 22b. The cable structure 30 is connected to the socket connector 34 by use of a cable connector 32 or board connector to be described later.

As the universal cord device 22 is connected to the processing apparatus 14, the camera module 24 is on-line with the processing apparatus 14 through the cable structure 30. The cable structure 30 is used for the processing apparatus 14 to supply power and transmit and receive signals, so that the processing apparatus 14 controls and drives the camera module 24 for imaging. When an image is obtained, the display panel 16 is driven by the processing apparatus 14 to display the image.

In FIG. 2, a flexible tube device 18b or tubular housing is attached to a proximal end of the tip device 18a. The flexible tube device 18b receives penetration of the cable structure 30. Originally, the flexible tube device 18b is prepared separately from the tip device 18a. After the cable structure 30 is penetrated into the flexible tube device 18b, the tip device 18a is attached to the flexible tube device 18b.

The cable connector 32 is disposed at a distal end of the cable structure 30. The cable structure 30 is penetrated into the flexible tube device 18b by advancing the cable connector 32. The cable connector 32 passes through the handle device 20 and the universal cord device 22 and reaches the connector shell 22b of the universal cord device 22. The cable connector 32 is mechanically coupled with (plugged in) the socket connector 34 disposed in the connector shell 22b.

The universal cord device 22 includes a cover tube (not shown) through which the universal cable portion and the light guide device extend.

Figure 3:
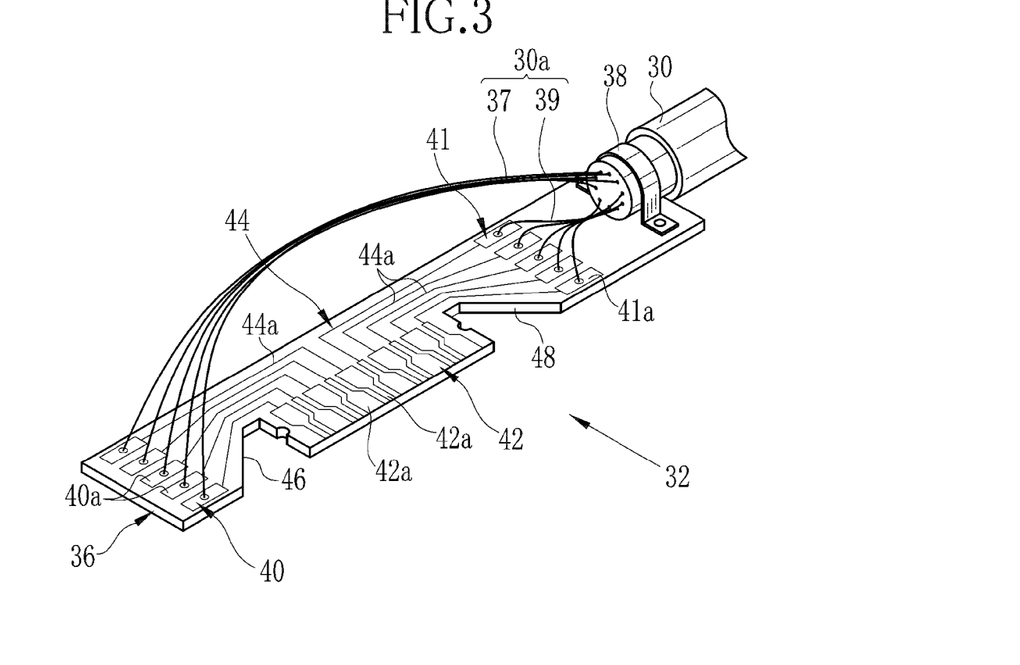
FIG. 3 is a perspective view illustrating the cable connector.

In FIG. 3, the cable connector 32 includes a circuit board 36 (substrate board) and a retainer 38 for retaining the cable structure 30 on the circuit board 36. The circuit board 36 is formed from rigid material. The circuit board 36 is a long plate extending in the axial direction, and has a smaller width than an inner diameter of the flexible tube device 18b for easy passage through the flexible tube device 18b.

A front end of the cable structure 30 is attached to a rear board end of the circuit board 36. The retainer 38 squeezes the cable structure 30 with an upper surface of the circuit board 36 for firm attachment. Plural electric lines 30a or wire lines constitute the cable structure 30. A first line group 37 in the cable structure 30 with the electric lines 30a is power supply lines for supplying the camera module 24 with power. A second line group 39 in the cable structure 30 is signal lines for transmitting and receiving a signal with the camera module 24.

Various circuit elements are mounted on the upper surface of the circuit board 36, including a first land pattern 40 in a multiple land form or land group, a second land pattern 41 (land group), a terminal group 42, and a wiring pattern 44. The first land pattern 40 is an array of first lands 40a disposed at a front board end of the circuit board 36. The second land pattern 41 is an array of second lands 41a disposed at the rear board end. The arrays are disposed to extend in the transverse direction of the circuit board 36.

The electric lines 30a are electrically coupled to the first and second lands 40a and 41a. In the present embodiment, power supply lines in the first line group 37 are coupled to the first lands 40a. Signal lines for transmission in the second line group 39 are coupled to the second lands 41a.

The terminal group 42 includes plural terminals 42a disposed between the first and second land patterns 40 and 41. The wiring pattern 44 includes plural conductive lines 44a printed on the upper surface of the circuit board 36. The terminals 42a are electrically coupled to the first and second lands 40a and 41a by the conductive lines 44a. In the embodiment, the terminals 42a are arranged along one longer side line of the circuit board 36. Several of the terminals 42a near to the front board end of the circuit board 36 are coupled to the first lands 40a. Several of the terminals 42a near to the rear board end are coupled to the second lands 41a.

To couple the cable connector 32 with the socket connector 34, the circuit board 36 is moved in a direction for advancing the terminal group 42, to enter the portion of the circuit board 36 having the terminal group 42 into the socket connector 34. Terminals (not shown) in the socket connector 34 come in contact with the terminals 42a to couple the cable connector 32 with the socket connector 34 for electrical conduction.

A protection packaging or cover (not shown) is disposed around the signal lines 30a for covering. An example of the protection packaging is a heat contraction tube or rubber tube. A portion of the protection packaging over the terminal pattern 42 has been open so that the terminal pattern 42 appears and is couplable to the socket connector 34. Note that an open portion may not be formed in the protection packaging. It is possible to remove the protection packaging entirely after entry of the cable connector 32 in the flexible tube device 18b without an open portion for the terminal pattern 42.

A pair of cutouts 46 and 48 are formed in the circuit board 36 and disposed on its longer side line. The cutouts 46 and 48 are arranged in the longitudinal direction of the circuit board 36, and operate for preventing interference of walls of the socket connector 34 in the course of coupling the cable connector 32 with the socket connector 34. The cutout 46 has a tapered shape with a surface inclined in a direction to increase its depth toward the center of the circuit board 36 in its transverse direction. The cutout 48 has a tapered shape with a surface inclined in a direction to increase its depth symmetrically with the cutout 46. Thus, the cutouts 46 and 48 guide the socket connector 34 toward a position of a predetermined depth of the circuit board 36 in the course of coupling the cable connector 32 with the socket connector 34 by plug-in.

In the cable connector 32, the first line group 37 with part of the electric lines 30a from the camera module 24 is coupled to the first land pattern 40. The second line group 39 with part of the electric lines 30a from the camera module 24 is coupled to the second land pattern 41. It is possible to couple two times as many electric lines to the circuit board 36 as a conventional circuit board where all of the electric lines are coupled to the second land pattern 41 at the rear board end of the circuit board 36.

In the cable structure 30 with the electric lines 30a, the first line group 37 for power supply is coupled to the first land pattern 40 disposed on the front side from the terminal group 42. The second line group 39 for transmission is coupled to the second land pattern 41 disposed on the rear side from the terminal group 42. It is possible in the cable connector 32 to prevent occurrence of crosstalk noise in the second line group 39 due to the first line group 37. An example of lines in the first line group 37 is a coaxial line. An example of lines in the second line group 39 is a wire line having a single wire.

The cutouts 46 and 48 in the circuit board 36 are effective in structurally reducing a width of the cable connector 32 in comparison with a cable connector in which a terminal group protrudes laterally from its longer side line. Also, the inner tapered shape of the cutouts 46 and 48 facilitates the mechanical coupling (plug-in) of the cable connector 32 with the socket connector 34, because the cutouts 46 and 48 can guide the cable connector 32 for the suitable depth to the socket connector 34 before the mechanical coupling.

Details of the construction of the invention are not limited to the embodiments. In the embodiments, the cable connector is mechanically coupled with the socket connector by directing the front board end of the circuit board to the processing apparatus. However, a cable connector may be mechanically coupled with a socket connector by directing a rear board end or lateral edge of a circuit board to the processing apparatus. In the above embodiments, the cable structure is entered in the elongated tube in a state with the cable connector. However, a cable connector can be combined with a cable structure after entering the cable structure in the elongated tube. Also, types of electric lines for coupling to each of the first and second land patterns can be changeable. It is possible to include a signal line for transmission among lines for coupling to the first land pattern, and include a power supply line among lines for coupling to the second land pattern. Lines for various purposes other than transmission and driving can be included in lines for coupling to each of the first and second land patterns.

Also, a circuit board (substrate board) for a cable connector can be a flexible wiring board. A portion of the flexible wiring board having the terminal group is preferably rigid for the purpose of facilitating mechanical coupling with a socket connector. Examples of methods of forming the rigid portion in the circuit board include a method of using a material for the rigid portion different from a material for its remaining portion, and a method of attaching a reinforcing plate to the rigid portion.

Figure 4:
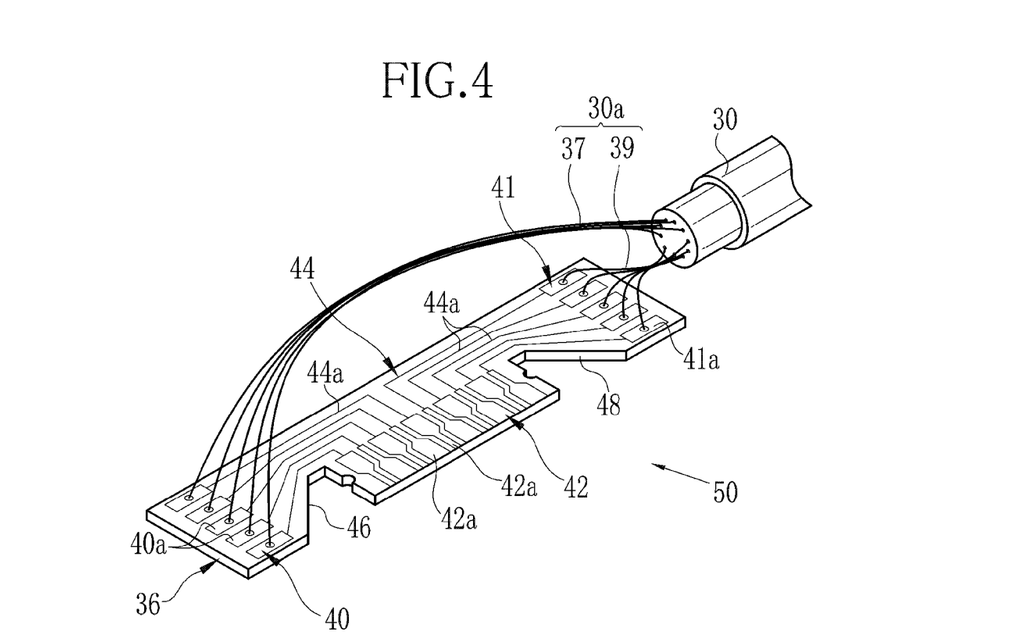
FIG. 4 is a perspective view illustrating another preferred cable connector without a retainer.

In FIG. 4, another preferred cable connector 50 or board connector has a feature of lack of the retainer 38. Elements similar to those of the above embodiments are designated with identical reference numerals.

Figure 5:
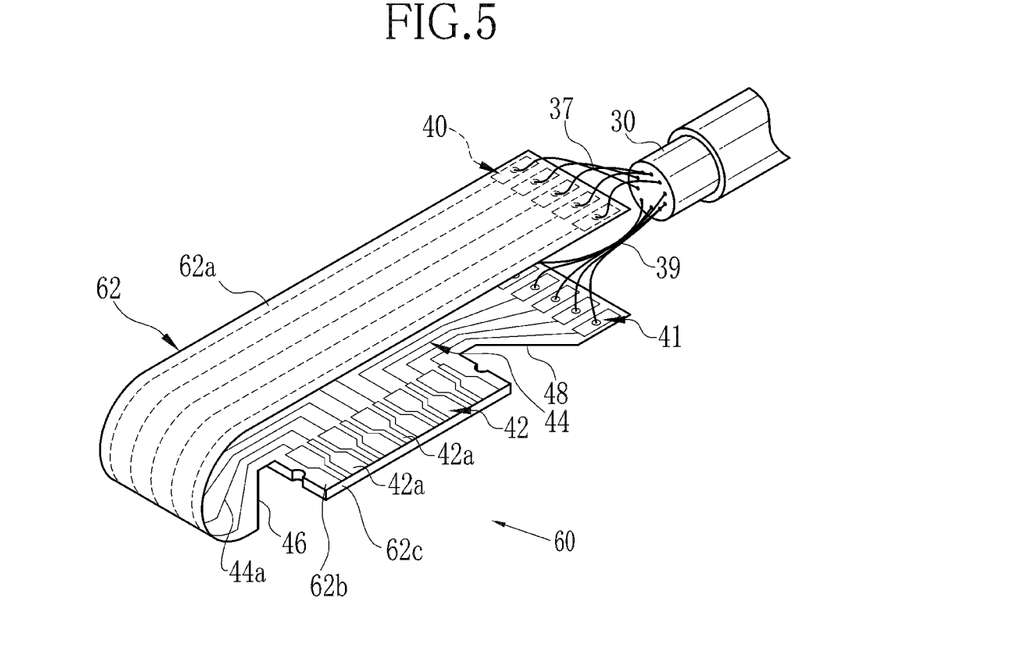
FIG. 5 is a perspective view illustrating one preferred cable connector with a flexible wiring board.

In FIG. 5, one preferred cable connector 60 is illustrated. A flexible wiring board 62 constitutes a circuit board in the cable connector 60, and is bent substantially in a U shape to direct ends of the flexible wiring board 62 toward the front end of the cable structure 30. A first portion 62a of the flexible wiring board 62 has the first land pattern 40. A second portion 62b of the flexible wiring board 62 has the second land pattern 41 and the terminal pattern 42 and opposed to the first portion 62a. A rigid plate 62c is attached to a lower surface of the portion of the terminal pattern 42 for reinforcement. The rigid plate 62c is effective in facilitating the mechanical coupling with the socket connector, and keeping reliable contact. Note that only a bend of the circuit board can be constituted by a small flexible wiring board instead of the use of the flexible wiring board 62 for the entirety of the circuit board. Upper and lower circuit boards are combined and interconnected by the small flexible wiring board at the bend.

Figure 6:
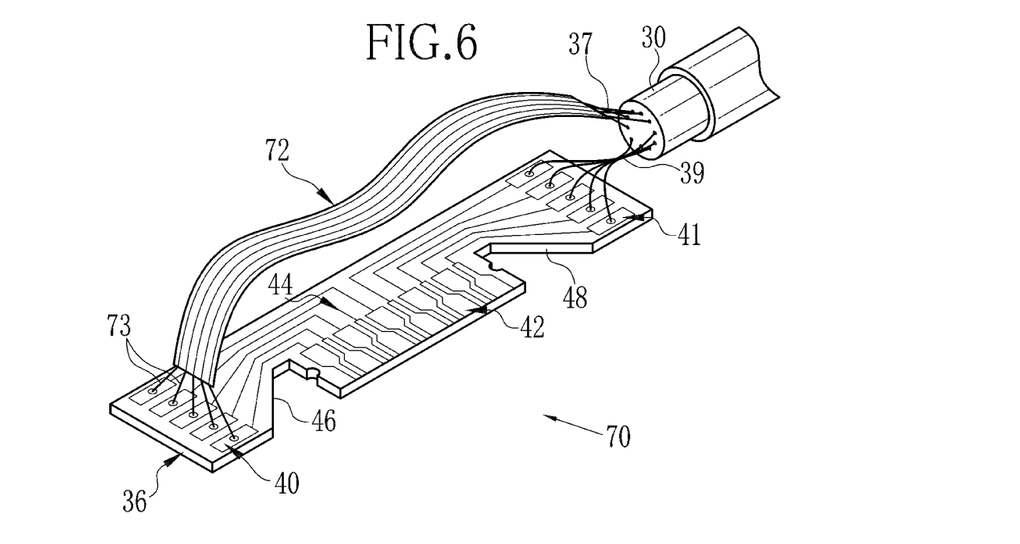
FIG. 6 is a perspective view illustrating still another preferred cable connector partially combined with a flexible wiring board.

In FIG. 6, still another preferred cable connector 70 or board connector includes a flexible wiring board 72 disposed between the first land pattern 40 of the circuit board 36 and the electric lines 30a of the first line group 37. Electric lines 73 couple the flexible wiring board 72 to the first land pattern 40. Furthermore, it is possible to form an additional wiring pattern (not shown) on the flexible wiring board 72, and couple the additional wiring pattern to the first lands 40a by soldering for discrete connection in place of using the electric lines 73. Also, the entirety or a part of electric lines for connection to the second land pattern 41 can be constituted by a flexible wiring board.

Figure 7:
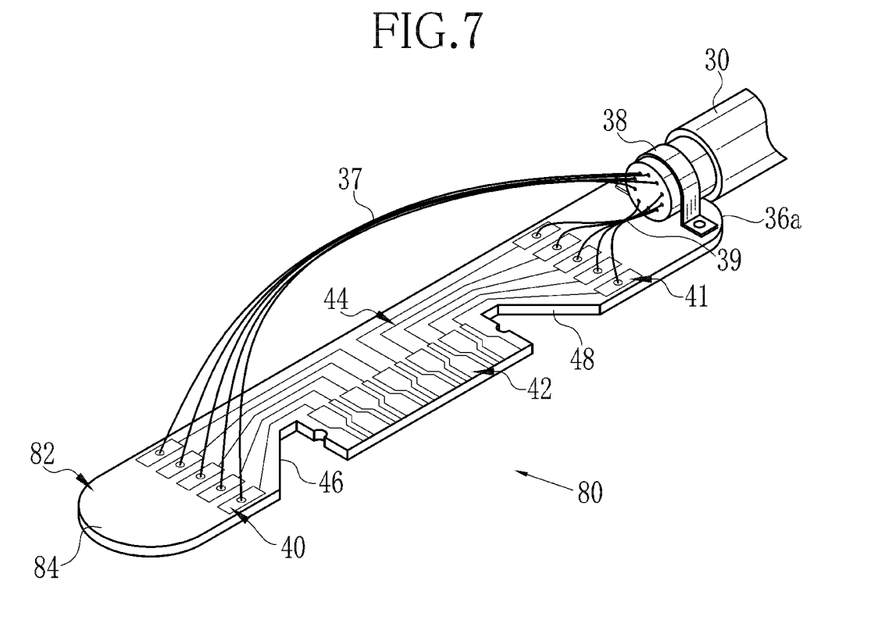
FIG. 7 is a perspective view illustrating one preferred cable connector with a tab portion.

In FIG. 7, one preferred cable connector 80 includes a circuit board 82 and a tab portion 84 with a curved edge for advance. The tab portion 84 is defined by extending the circuit board 82 in the forward direction on the side of the first land pattern 40. The tab portion 84 has a shape with a decreasing width in the forward direction for reducing resistance of the flexible tube device 18b for entry. The tab portion 84 prevents the first land pattern 40 of the circuit board 82 from being damaged or scratched in the course of passage through the flexible tube device 18b.

A tapered guide surface 36a is formed at a rear board end of the cable connector 80, curved arcuately, and utilized for guiding in the course of disassembling the cable connector 80. The cable connector 80 can be pulled and disassembled safely by use of the guide surface 36a for the purpose of maintenance, because the guide surface 36a prevents the cable connector 80 from interference with the inner surface of the flexible tube device 18b. The guide surface 36a is illustrated only in FIG. 7, but can be formed in the corresponding portion in each of all the embodiments.

Note that the shape of the tab portion 84 is not limited and can be changed suitably. Also, the tab portion 84 can be originally separate from the circuit board 82, and can be attached to its front board end. For example, the tab portion 84 can be in a form of a cap.

Figure 8:
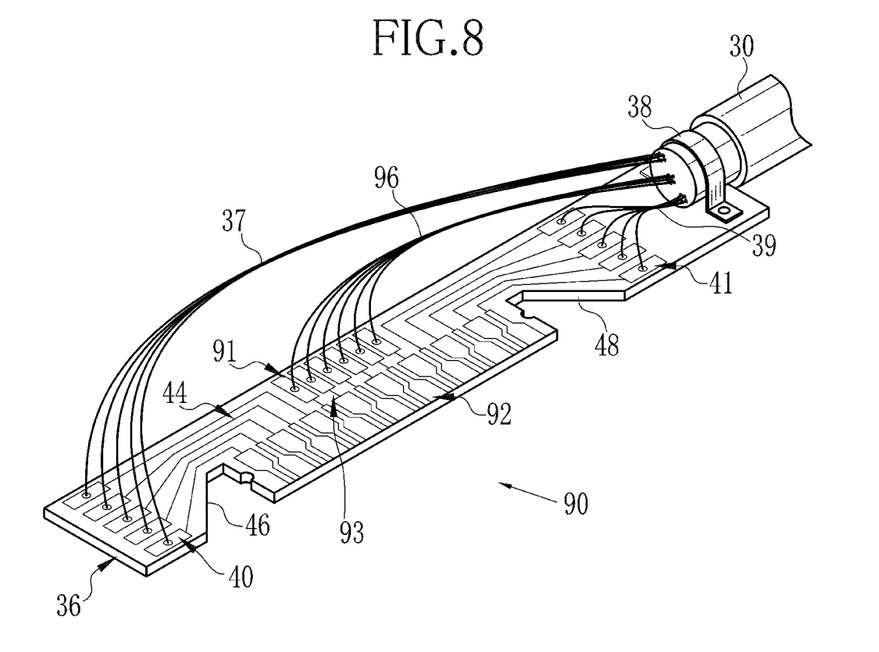
FIG. 8 is a perspective view illustrating another preferred cable connector with a third land pattern.

In FIG. 8, another preferred cable connector 90 or board connector includes a third land pattern 91 (land group) disposed between the first and second land patterns 40 and 41. A terminal group 92 is disposed along one longer side line opposite to another longer side line where the third land pattern 91 extends. A third line group 96 with the electric lines 30a can be electrically coupled to the third land pattern 91. A second wiring pattern 93 is disposed between the third land pattern 91 and the terminal group 92. The terminal group 92 has terminals 92a. The third land pattern 91 has conductive lands 91a, which are coupled to the terminals 92a by the second wiring pattern 93.

Figure 9:
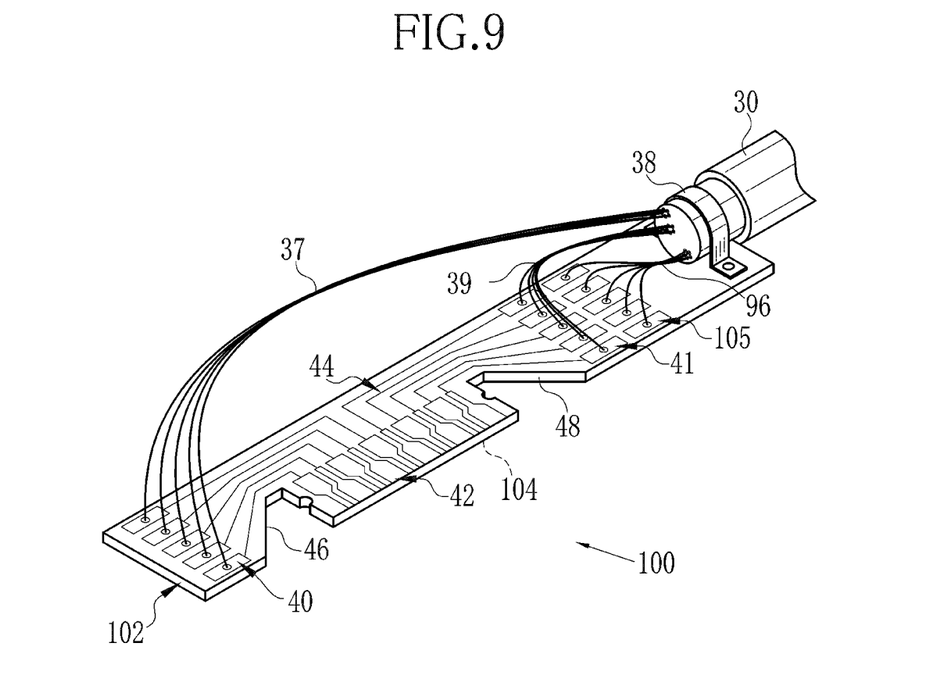
FIG. 9 is a perspective view illustrating one preferred cable connector with a second terminal group on a lower surface.
Figure 10:
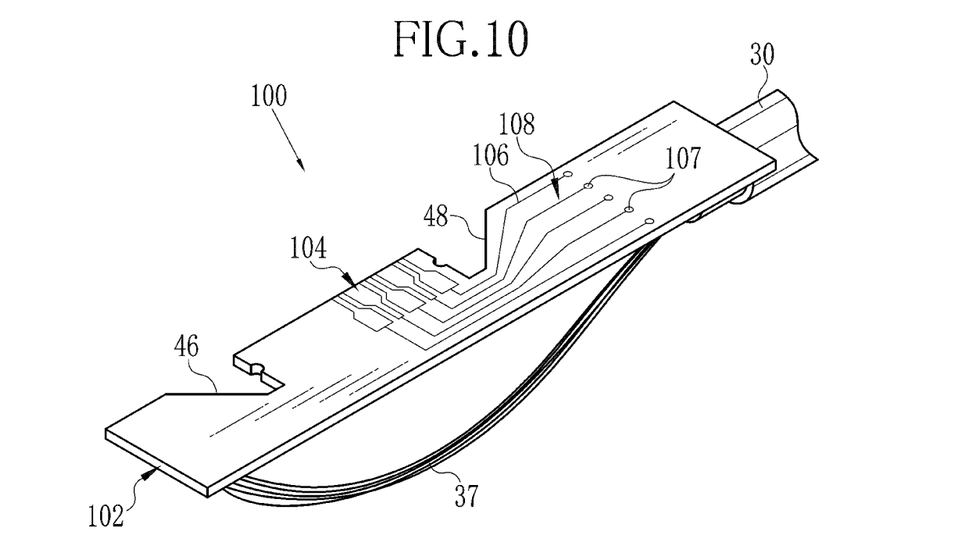
FIG. 10 is a bottom perspective view illustrating the cable connector.

In FIGS. 9 and 10, one preferred cable connector 100 includes a circuit board 102. A second terminal group 104 is mounted on a lower surface of the circuit board 102. In FIG. 9, a third land pattern 105 (land group) is mounted on the upper surface of the circuit board 102 and positioned on the rear side from the second land pattern 41. The third line group 96 with the electric lines 30a is electrically coupled to the third land pattern 105.

In FIG. 10, a second wiring pattern 108 in the cable connector 100 includes conductive lines 106 and through hole vias 107. The conductive lines 106 are printed on a lower surface of the circuit board 102. The through hole vias 107 are formed through the circuit board 102. In the cable connector 100, the second wiring pattern 108 electrically couples the second terminal group 104 to the third land pattern 105. Note that it is possible to form cutouts, holes (not shown) or the like in the circuit board 102 for penetration of the electric lines 30a, and to couple the electric lines 30a to the third land pattern 105.

Furthermore, an auxiliary land pattern may be added on the upper surface and on the front side from the first land pattern 40, and electrically coupled to a second terminal group on the lower surface of the circuit board. Namely, the auxiliary land pattern in the cable connector can be disposed on a side opposite to the third land pattern 105 in the cable connector 100 in FIGS. 9 and 10 in the axial direction. Also, a subsidiary land pattern may be disposed on the upper surface and near to the third land pattern 91 of FIG. 8, and electrically coupled to a second terminal group on the lower surface of the circuit board. Two or more of types of the third land pattern 105, the auxiliary land pattern and the subsidiary land pattern can be combined in a form coupled to a second terminal group on the lower surface by wiring through the circuit board.

Figure 11:
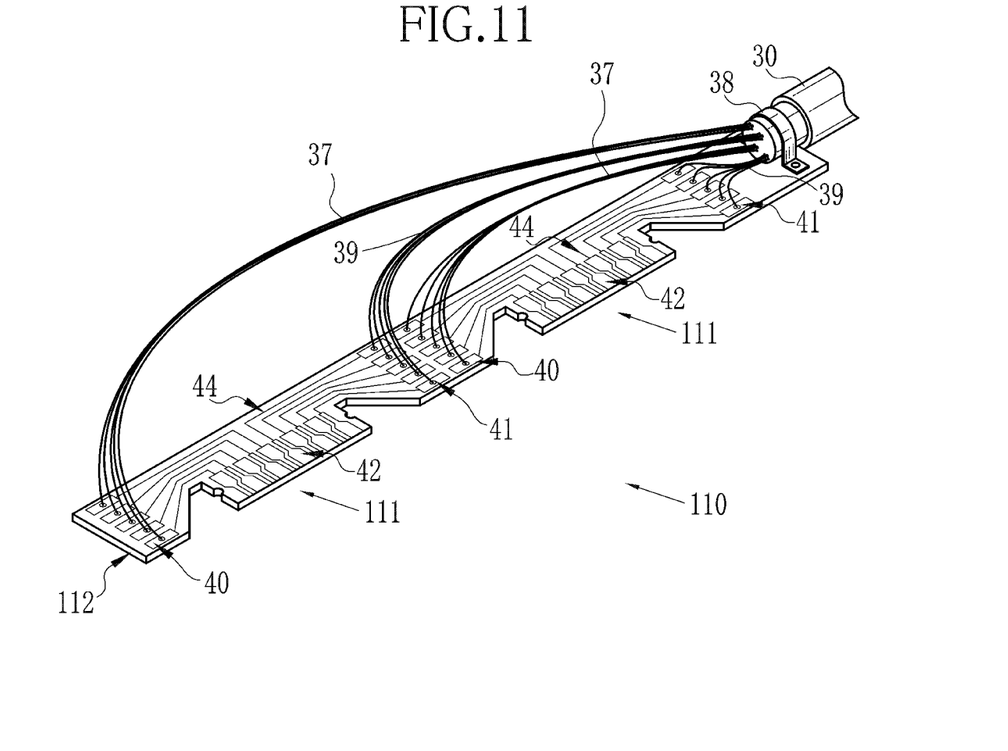
FIG. 11 is a perspective view illustrating still another preferred cable connector with two terminal groups arranged serially.

In FIG. 11, still another preferred cable connector 110 or board connector has a circuit board 112 with two sets of the terminal groups 42. The first land pattern 40 is disposed on each of the terminal groups 42. The second land pattern 41 is disposed on each of the terminal groups 42. In short, the cable connector 110 has two connection mechanisms 111 in an array. Also, three or more terminal groups 42 may be disposed on a circuit board. The first and second land patterns 40 and 41 may be disposed in the manner of FIG. 11. It is possible to mount conductive elements in the cable connector 110 at a high density, as the number of the electric lines 30a in combination with each one of the terminal patterns 42 can be high.

The embodiment of the cable connector 110 having the two connection mechanisms is used for simultaneous coupling of two socket connectors 34. Also, selective use of the connection mechanisms is possible. One of those is selectively connected with the socket connector 34. A remaining one of those is normally unused and reserved for an auxiliary use.

Figure 12:
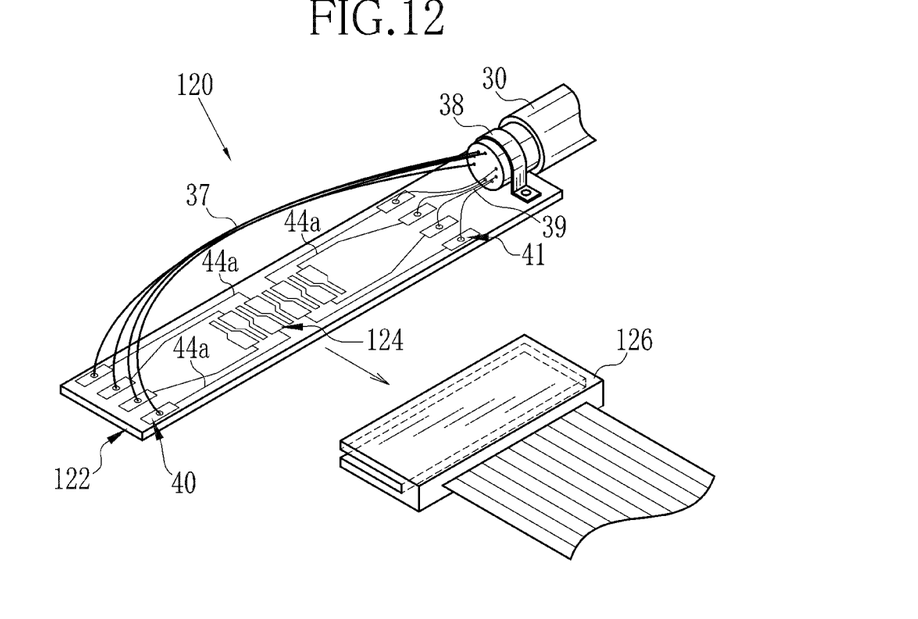
FIG. 12 is a perspective view illustrating one preferred cable connector with the terminal group disposed in the center.

In FIG. 12, one preferred cable connector 120 has a circuit board 122. A terminal group 124 is disposed at the center of the circuit board 122 in the transverse direction. For use with the terminal group 124, a socket connector 126 or mating connector has a fork shape with upper and lower ridges for capturing the circuit board 122 between those for coupling to the terminal group 124.

Figure 13:
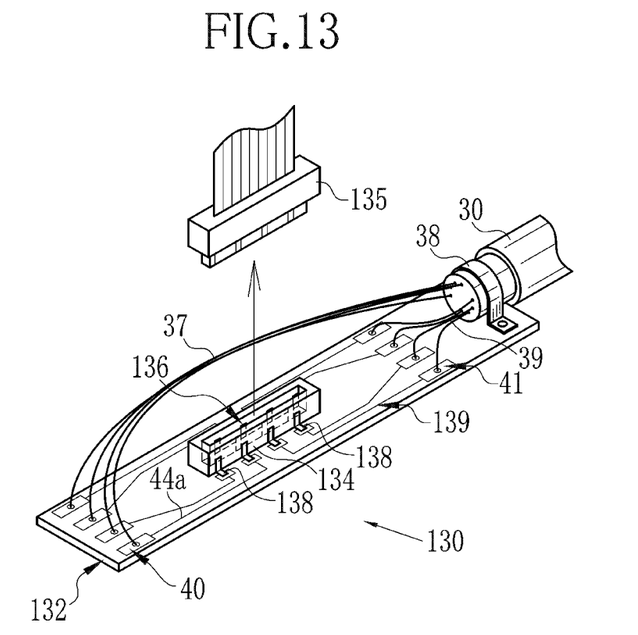
FIG. 13 is a perspective view illustrating another preferred cable connector with a ridge projection of a socket shape in which the terminal group is disposed.

In FIG. 13, another preferred cable connector 130 includes a circuit board 132, a terminal group 136 and a ridge projection 134 with a slot terminal. The ridge projection 134 is disposed at the center of the circuit board 132. The terminal group 136 is mounted inside the ridge projection 134 of a socket shape. Conductive lands 138 are mounted in the ridge projection 134 to extend to respectively terminals in the terminal group 136. A wiring pattern 139 is electrically coupled to the conductive lands 138. A socket connector 135 or mating connector is set above the circuit board 132. The cable connector 130 is moved up to the socket connector 135 for engaging the ridge projection 134 with the socket connector 135.

Figure 14:
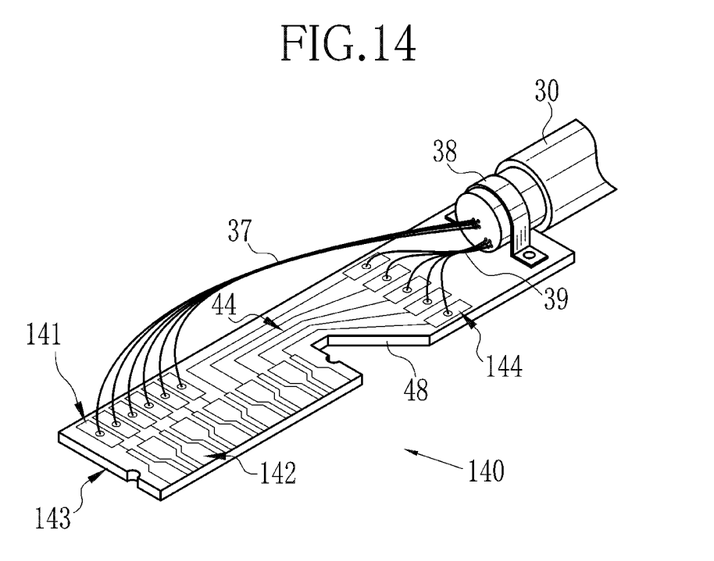
FIG. 14 is a perspective view illustrating one preferred cable connector with only one cutout.
Figure 15:
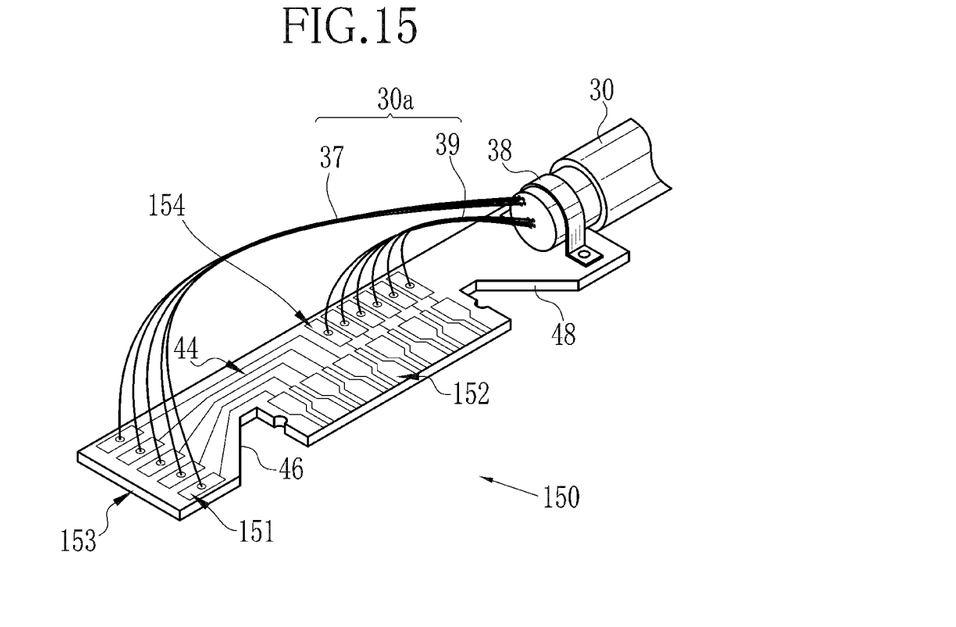
FIG. 15 is a perspective view illustrating still another preferred cable connector in which a second land pattern is directed in the axial direction.

According to the invention, the first and second land patterns are arranged so that at least part of the terminal group is disposed between those in the axial direction. Furthermore, the first and second land patterns are arranged in the longitudinal direction of the circuit board in any sequence. It is unnecessary to dispose the first land pattern at the front board end or dispose the second land pattern at the rear board end. For example, a cable connector 140 of FIG. 14 has a first land pattern 141 in a multiple land form or land group, and a second land pattern 144 (land group). The first land pattern 141 extends along one longer side line of a circuit board 143, and is positioned opposite to a terminal group 142 on the circuit board 143 in the transverse direction. The second land pattern 144 is disposed at the rear board end of the circuit board 143 with respect to the terminal group 142. In FIG. 15, one preferred cable connector 150 has a first land pattern 151 in a multiple land form or land group, and a second land pattern 154 (land group). The first land pattern 151 is positioned at the front board end of a circuit board 153 with respect to a terminal group 152. The second land pattern 154 extends along one longer side line of the circuit board 153, and is arranged with the terminal group 152 in the transverse direction.

Figure 16:
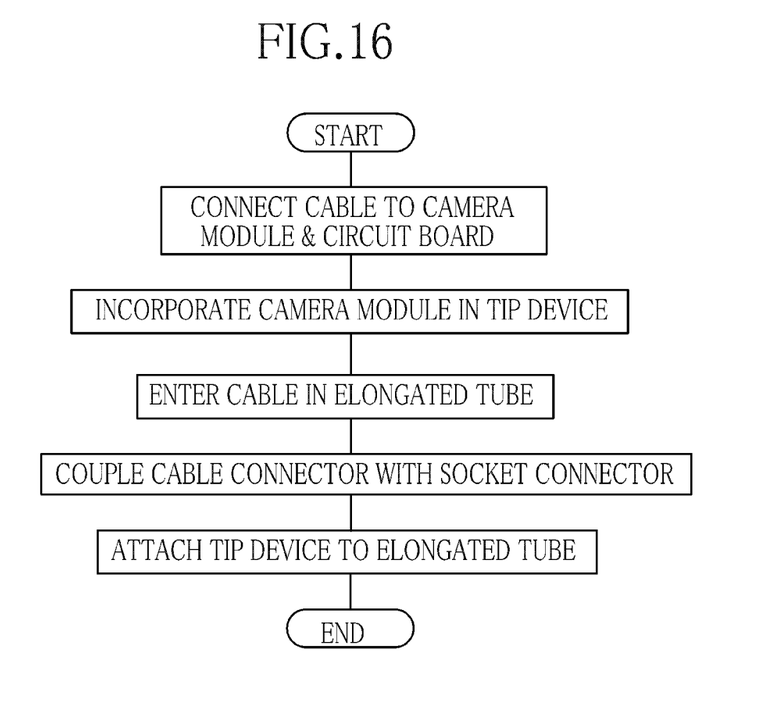
FIG. 16 is a flow chart illustrating a method of producing the endoscope apparatus.

In FIG. 16, production of the endoscope apparatus with the cable connector is illustrated. At first, first tips of the electric lines 30a of the cable structure 30 are coupled to a circuit board of a camera module as a circuit device by soldering. In FIG. 3, second tips (front) of the electric lines 30a are electrically coupled to the first and second lands 40a and 41a of the cable connector 32. The retainer 38 is used as required, and firmly retains the cable structure 30 to the circuit board 36.

The camera module 24 becomes incorporated in the tip device 18a. See FIG. 2. Then the cable connector 32 is advanced and entered in the flexible tube device 18b. A pull wire (not shown) is used and has been penetrated in the flexible tube device 18b. A first end of the pull wire is firmly fastened to a portion of the circuit board 36 at the cutout 46, and connected to the cable connector 32. A second end of the pull wire is pulled manually to penetrate the cable connector 32 through the flexible tube device 18b.

After the cable structure 30 is penetrated through the flexible tube device 18b, the socket connector 34 is coupled with the terminal pattern 42 connectively. Then the flexible tube device 18b is attached to the tip device 18a.

Note that the position of the coupling between the cable connector and the socket connector (mating connector) is changeable with high degree of freedom. It is possible in the invention to couple the cable connector with a socket connector in the handle, the light source apparatus, or the processing apparatus. Also, a circuit board (substrate board) in the cable connector is not limited to the plate shape, but can be in a cylindrical or prismatic shape or the like.

An example of the cable connector 32 for the light source apparatus 13 is described now. As is not shown in FIG. 2, the light guide device is penetrated through the elongated tube 18 and the universal cord device 22 together with the cable structure 30. The terminal group 42 is oriented in the transverse direction vertical to the axial direction. At the left end of FIG. 2, the light guide device extends in the axial direction. This is contained in the connector shell 22a of the universal cord device 22 in FIG. 1, and becomes coupled optically with an internal light guide device for the light source by plug-in to a socket of the light source apparatus 13 in the axial direction.

Figure 17:
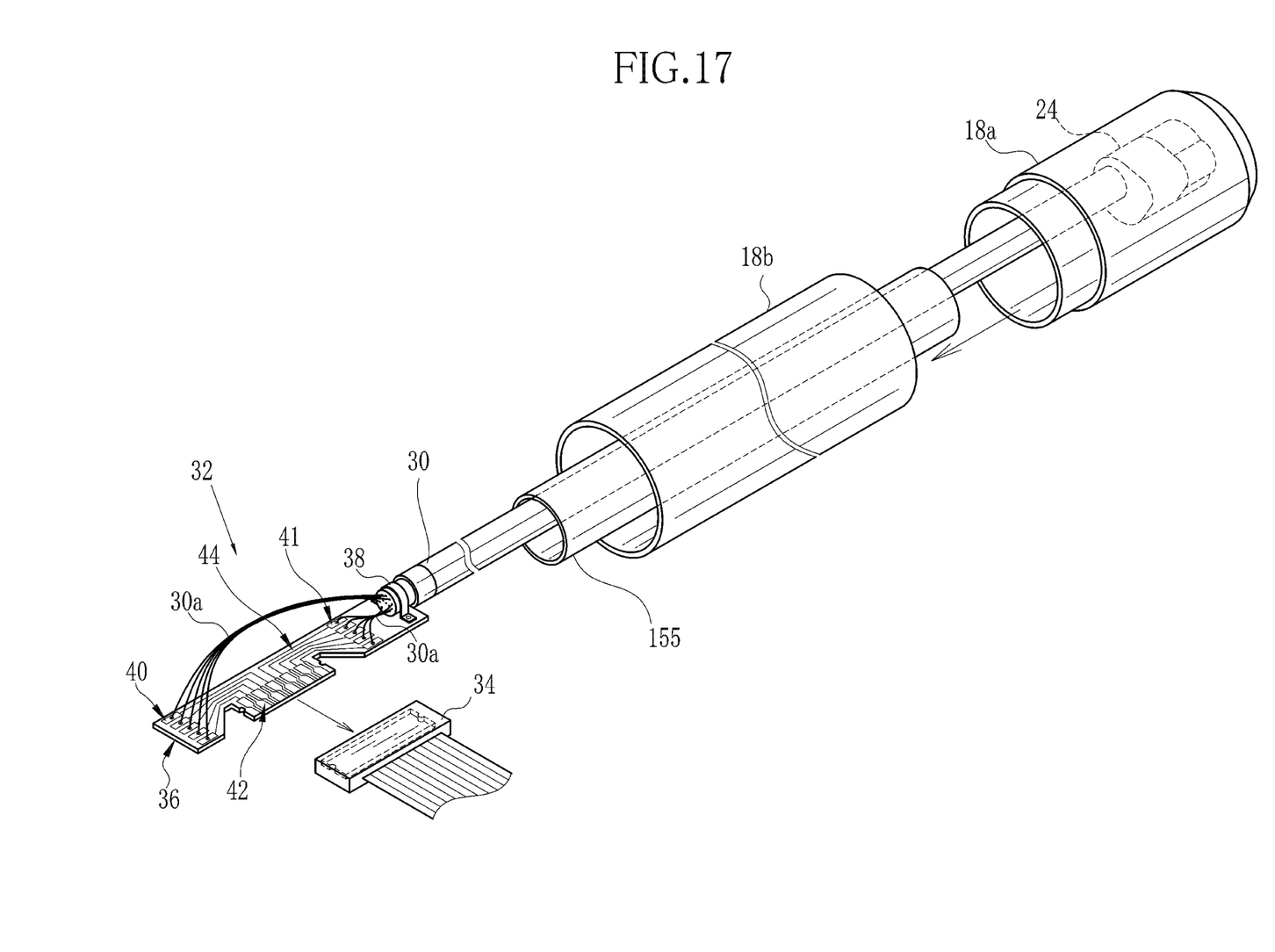
FIG. 17 is a perspective view illustrating the cable structure, the elongated tube and the socket connector in combination with a protection tube.

Although the cable connector 32 and the cable structure 30 are directly penetrated through the elongated tube 18 in the above embodiments, the cable connector 32 and the cable structure 30 can be passed through a protection tube 155 of FIG. 17, working channel or the like provided in the elongated tube 18. For this structure, the cable connector 32 and the cable structure 30 can be entered directly in the protection tube 155, working channel or the like without a guide mechanism, because the resiliency of the cable structure 30 can be utilized.

In the above embodiments, the camera module 24 is incorporated in the tip device 18a. However, the camera module 24 may be incorporated in a portion of the elongated tube 18 on a proximal side from the tip device 18a. For this structure, an imaging window, a lens, a light guide device and the like are incorporated in the tip device 18a for receiving object light.

In the above embodiments, the endoscope apparatus includes the camera module for imaging optically. However, a tube apparatus of the invention may be an ultrasonic endoscope having an ultrasonic transducer, catheter, probe or the like. An endoscope apparatus of the invention may be for industrial use without medical use. Also, a cable connector may be used for a device of various types other than an endoscope apparatus, and can be used with a cable passed through a tube of a small diameter.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A cable connector for an endoscope apparatus including a flexible elongated tube for extending in an axial direction, a circuit device incorporated in said elongated tube, a cable structure, having plural electric lines, contained in said elongated tube, connected with said circuit device, wherein said cable connector is mounted on said cable structure, and couplable with an external socket connector for externally transmitting a signal from said circuit device, said cable connector comprising:
   a circuit board, having a width in a manner passable through said elongated tube, disposed to extend in said axial direction;
   a terminal group of plural terminals, formed on said circuit board, for electrically contacting said socket connector;
   first and second land patterns, positioned apart from one another in said axial direction, so disposed that said terminal group is positioned therebetween at least partially, for electrical conduction to said electric lines;
   a wiring pattern, formed on said circuit board, for electrically coupling said first land pattern to said terminal group and electrically coupling said second land pattern to said terminal group.

2. A cable connector as defined in claim 1, wherein said first land pattern is disposed on a side of a first board end of said circuit board from said terminal group in said axial direction;
   said second land pattern is disposed on a side of a second board end of said circuit board from said terminal group in said axial direction;
   said terminal group is constituted in said axial direction by a first terminal on said side of said first board end, and a second terminal on said side of said second board end;
   said wiring pattern is constituted in said axial direction by a first conductive line on said side of said first board end, and a second conductive line on said side of said second board end;
   said first conductive line couples said first terminal to said first land pattern;
   said second conductive line couples said second terminal to said second land pattern.

3. A cable connector as defined in claim 1, wherein said elongated tube includes:
   a flexible tube device for extending in said axial direction;
   a tip device mounted on a tip end of said flexible tube device;

wherein said tip device is attached to said flexible tube device after said cable structure is entered through said flexible tube device.

4. A cable connector as defined in claim 1, wherein said terminals in said terminal group are arranged in said axial direction.

5. A cable connector as defined in claim 4, wherein said terminal group and said socket connector are moved relatively toward one another transversely to said axial direction, for contact of said terminal group with said socket connector.

6. A cable connector as defined in claim 5, wherein said terminals are arranged along a first longer side line of said circuit board, and said wiring pattern is disposed between said terminal group and a second longer side line of said circuit board.

7. A cable connector as defined in claim 6, further comprising a pair of cutouts, formed in said circuit board, disposed on said first longer side line so that said terminal group is positioned therebetween, for receiving said socket connector upon entry of said terminal group in said socket connector, to prevent interference with said circuit board.

8. A cable connector as defined in claim 7, wherein said cutouts are so shaped that a width thereof decreases toward a center portion of said circuit board from said longer side line.

9. A cable connector as defined in claim 1, wherein said electric lines include:
   a power supply line for driving said circuit device;
   a signal line for transmitting and/or receiving said signal with said circuit device;
   said power supply line being coupled to said first land pattern, and said signal line being coupled to said second land pattern.

\* \* \* \* \*